(12) United States Patent
Gottardi et al.

(10) Patent No.: US 12,070,475 B2
(45) Date of Patent: Aug. 27, 2024

(54) EXTRACTS FOR THE REGENERATION OF LIGAMENTS

(71) Applicants: University of Pittsburgh—Of the Commonwealth System of Higher Education, Pittsburgh, PA (US); Ri.MED Foundation, Palermo (IT)

(72) Inventors: Riccardo Luca Gottardi, Pittsburgh, PA (US); Benjamin Burke Rothrauff, Pittsburgh, PA (US); Rocky Sung Chi Tuan, Pittsburgh, PA (US); Shinsuke Kihara, Pittsburgh, PA (US)

(73) Assignees: University of Pittsburgh—Of the Commonwealth System of Higher Education, Pittsburgh, PA (US); Ri.MED Foundation (IT)

( * ) Notice: Subject to any disclaimer, the term of this patent is extended or adjusted under 35 U.S.C. 154(b) by 1037 days.

(21) Appl. No.: 16/970,861

(22) PCT Filed: Feb. 22, 2019

(86) PCT No.: PCT/US2019/019119
§ 371 (c)(1),
(2) Date: Aug. 18, 2020

(87) PCT Pub. No.: WO2019/165185
PCT Pub. Date: Aug. 29, 2019

(65) Prior Publication Data
US 2020/0368289 A1    Nov. 26, 2020

Related U.S. Application Data

(60) Provisional application No. 62/633,746, filed on Feb. 22, 2018.

(51) Int. Cl.
| | | |
|---|---|---|
| A61K 36/00 | (2006.01) | |
| A61K 9/19 | (2006.01) | |
| A61K 35/32 | (2015.01) | |
| A61K 47/18 | (2017.01) | |

(52) U.S. Cl.
CPC ............... *A61K 35/32* (2013.01); *A61K 9/19* (2013.01); *A61K 47/18* (2013.01)

(58) Field of Classification Search
None
See application file for complete search history.

(56) References Cited

U.S. PATENT DOCUMENTS

| | | |
|---|---|---|
| 8,361,503 B2 | 1/2013 | Badylak et al. |
| 8,535,719 B2 | 9/2013 | Badylak et al. |
| 8,691,276 B2 | 4/2014 | Badylak et al. |
| 9,237,945 B2 | 1/2016 | El-Kurdl et al. |
| 2004/0078077 A1 | 4/2004 | Binnette et al. |
| 2014/0377213 A1 | 12/2014 | Hong et al. |
| 2015/0010510 A1 | 1/2015 | Badylak et al. |
| 2016/0166735 A1 | 6/2016 | Chang et al. |
| 2017/0173217 A1 | 6/2017 | Badylak et al. |

FOREIGN PATENT DOCUMENTS

| | | |
|---|---|---|
| EP | 1410810 B1 | 4/2004 |
| WO | 2014144215 A1 | 9/2014 |
| WO | 2017123883 A1 | 7/2017 |

OTHER PUBLICATIONS

Blaudez et al. (2020) Methods 171: 28-40. (Year: 2020).*
Cheng et al. (2014) Biotechnology Advances 32: 462-484. (Year: 2014).*
Vavken et al. (2009) J. Orthoped. Res. 27: 1612-1618. (Year: 2009).*
Birch et al., "Specialisation of extracellular matrix for function in tendons and ligaments", Muscles, Ligaments and Tendons Journal, 2013, pp. 12-22, vol. 3(1).
Ding et al., "Extended-Release and Targeted Drug Delivery Systems", Remington The Science and Practice of Pharmacy, Lippincott Williams and Wilkins, 2006, pp. 939-964, Chapter 47.
Hong et al., "Tailoring the degradation kinetics of poly(ester-carbonate urethane)urea thermoplastic elastomers for tissue engineering scaffolds", Biomaterials, 2010, pp. 4249-4258, vol. 31(15).
"Polymers for Drug Delivery", Labco L.L.C., 12 pages.
Rothrauff et al., "Anatomical region-dependent enhancement of 3-dimensional chondrogenic differentiation of human mesenchymal stem cells by soluble meniscus extracellular matrix", Acta Biomaterialia, 2017, pp. 140-151, vol. 49.
Rothrauff et al., "Efficacy of thermoresponsive, photocrosslinkable hydrogels derived from decellularized tendon and cartilage extracellular matrix for cartilage tissue engineering", Journal of Tissue Engineering and Regenerative Medicine, 2018, pp. e159-e170, vol. 12.
Rothrauff et al., "Tissue-specific bioactivity of soluble tendon-derived and cartilage-derived extracellular matrices on adult mesenchymal stem cells", Stem Cell Research and Therapy, 2017, 8:133, 17 pages.
Shimomura et al., "Region-Specific Effect of the Decellularized Meniscus Extracellular Matrix on Mesenchymal Stem Cell-Based Meniscus Tissue Engineering", The American Journal of Sports Medicine, 2016, pp. 604-611, vol. 45, No. 3.
Singh et al., "Nanoparticle-based targeted drug delivery", Experimental and Molecular Pathology, 2009, pp. 215-223, vol. 86(3).
Wade et al., "Engineering ECM signals into biomaterials", Materials Today, 2012, pp. 454-459, vol. 15, No. 10.
Yang et al., "Enhancement of tenogenic differentiation of human adipose stem cells by tendon-derived extracellular matrix", Biomaterials, 2013, pp. 9295-9306, vol. 34.
Yang et al., "Tendon and Ligament Regeneration and Repair: Clinical Relevance and Developmental Paradigm", Birth Defects Research Part C: Embryo Today, 2013, pp. 203-222, vol. 99(3).
Yang et al., "Tendon-Derived Extracellular Matrix Enhances Transforming Growth Factor-beta3-Induced Tenogenic Differentiation of Human Adipose-Derived Stem Cells", Tissue Engineering: Part A, 2017, pp. 166-176, vol. 23, Nos. 3 and 4.

(Continued)

*Primary Examiner* — Russell G Fiebig
(74) *Attorney, Agent, or Firm* — The Webb Law Firm

(57) ABSTRACT

Provided herein is a ligament ECM soluble fraction useful for the growth and regrowth of ligament tissue. Methods of preparation of the soluble fractions and use of the soluble fractions in growth or regrowth of ligament tissue also are provided.

19 Claims, 3 Drawing Sheets

(56) References Cited

OTHER PUBLICATIONS

Yu et al., "Design of Nanoparticle-Based Carriers for Targeted Drug Delivery", Journal of Nanomaterials, 2016, 26 pages.

* cited by examiner

EXTRACTS FOR THE REGENERATION OF LIGAMENTS

CROSS REFERENCE TO RELATED APPLICATIONS

This application is the United States national phase of PCT/US2019/019119 filed Feb. 22, 2019, which claims the benefit of U.S. Provisional Patent Application No. 62/633,746, filed Feb. 22, 2018, each of which is incorporated herein by reference in its entirety.

The anterior cruciate ligament (ACL) is the most commonly injured knee ligament, with between 100,000 and 200,000 ACL ruptures per year in the U.S.A., and an annual incidence of approximately 1 in 3,500. Today, for ACL tear, the most established treatment is reconstruction which requires the sacrifice of a healthy tendon of the patient for an autograft procedure. On the other hand, isolated posterior cruciate ligament (PCL) or medial cruciate ligament (MCL) injury repaired with a conservative treatment showed good result even 10 years after surgery.

Difference in outcomes and healing between ACL and PCL has been widely discussed in the literature focusing on their anatomical differences (PCL is closer to the surrounding soft tissue and has a larger insertion area compared to ACL) on the kinematics stresses they are subject to (PCL lower stress position occurs during knee extension which is more commonly maintained in everyday life). However, there is little knowledge about any biological difference in relation to their regeneration and ACL and PCL are generally regarded as biologically very similar.

Avulsion of permanent teeth is one of the most common dental emergencies with over 5 million cases each year, especially in children and young adults, frequently as a consequence of sport trauma, with associated costs of care that exceeds $500 million. Tooth reinsertion has low success rates (as high as 50%) when occurring after 30 minutes of avulsion, a key limitation being the repair of the periodontal ligament that secures and stabilizes the tooth in the alveolar socket and that is completely torn in avulsion. Thus, patients are required to undergo expensive dental implant and/or prosthodontic therapies to restore function and appearance.

Therapeutic compositions that are useful in the repair or replacement of ligaments, or accelerating the healing of ligaments, such as the ACL, PCL, MCL, meniscofemoral ligament, and the periodontal ligament, as well as other ligaments, e.g., of the hip, ankle shoulder (e.g., rotator cuff), wrist, elbow, spine, knee, face, neck, etc., are desired.

SUMMARY

In one aspect, a method of inducing growth of ligament or tendon tissue in a patient is provided. The method comprises administering to the patient at a site of ligament or tendon damage or defect, a composition comprising a soluble fraction of decellularized, nuclease-digested ligament tissue (soluble fraction) in an amount effective to induce growth of a ligament or tendon in a patient.

In another aspect, a method of generating or regenerating a ligament structure in a patient is provided. The method comprising: implanting a ligament structure in a patient; and applying a composition comprising a soluble fraction of decellularized, nuclease-digested ligament tissue to a surface of the ligament structure, or adjacent to the ligament structure, in an amount effective to stimulate growth of a ligament.

In a further aspect, a pharmaceutical composition is provided, comprising a urea-soluble fraction of decellularized, nuclease-digested ligament tissue, and a pharmaceutically-acceptable excipient.

In yet another aspect, a ligament structure is provided. The structure comprises a cell growth scaffold that is optionally anisotropic, and a urea-soluble fraction of nuclease-digested, decellularized ligament tissue, such as cruciate ligament tissue or posterior cruciate ligament tissue.

In yet another aspect, a method of preparing a composition for stimulating ligament growth is provided, as well as a soluble fraction prepared according to the method. The method comprises:
  comminuting ligament tissue;
  decellularizing the tissue in a detergent or emulsifier, for example in a non-ionic detergent such as TRITON X-100, e.g., at 1% in water;
  digest nucleic acid in the decellularized tissue by treatment of the decellularized tissue with a nuclease, such as a DNAse or an RNAse;
  dissociating soluble components from insoluble components by exposure of the sample to a protein solubilizing reagent, such as urea, a guanidinium salt, thiourea, sodium dodecyl sulfate, a strong base, or a strong acid, for example, 1M to 8M urea, for example 3M urea in water;
  fractionating the composition, e.g., by centrifugation or chromatography, to separate a soluble fraction from insoluble fibrillar collagen, and collecting the soluble fraction, such as the supernatant; and
  removing the denaturant from the soluble fraction, e.g., by dialyzing against water or by column chromatography, such as by size-exclusion chromatography.

In yet another aspect, a kit is provided, comprising a composition comprising a solubilized fraction of decellularized, nuclease-digested ligament tissue in a vessel, such as a vial or medical syringe, wherein the composition is optionally lyophilized.

BRIEF DESCRIPTION OF THE DRAWINGS

The provided figures are illustrative of aspects of the present invention.

DETAILED DESCRIPTION

Figure 1:
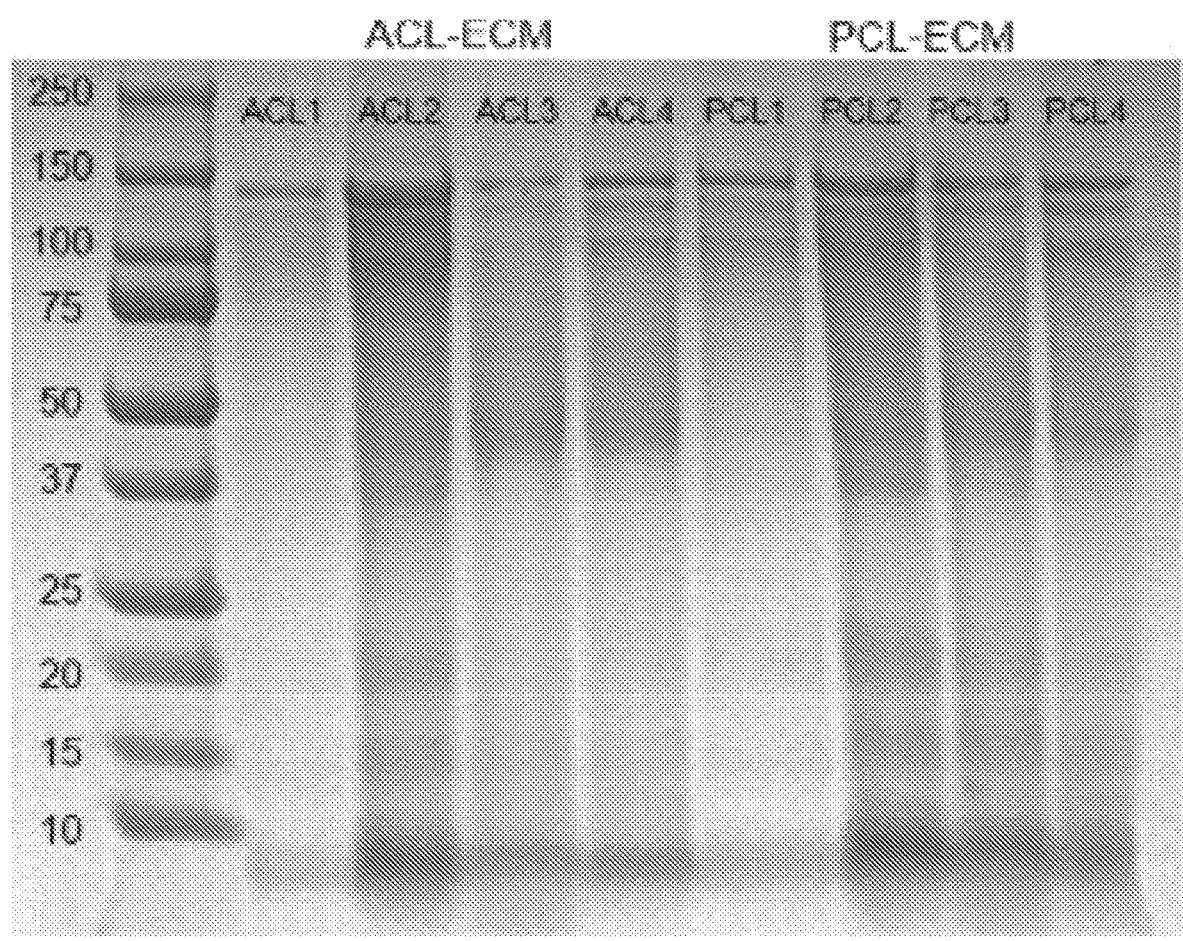
FIG. 1. Photograph of SDS-PAGE assay results, as described in Example 1.

Other than in the operating examples, or where otherwise indicated, the use of numerical values in the various ranges specified in this application are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of ranges is intended as a continuous range including every value between the minimum and maximum values. As used herein "a" and "an" refer to one or more.

As used herein, the term "comprising" is open-ended and may be synonymous with "including", "containing", or "characterized by". The term "consisting essentially of" limits the scope of a claim to the specified materials or steps and those that do not materially affect the basic and novel characteristic(s) of the claimed invention. The term "consisting of" excludes any element, step, or ingredient not specified in the claim. As used herein, embodiments "comprising" one or more stated elements or steps also include, but are not limited to embodiments "consisting essentially of" and "consisting of" these stated elements or steps. For definitions provided herein, those definitions refer to word forms, cognates and grammatical variants of those words or phrases.

As used herein, the terms "patient" or "subject" refer to members of the animal kingdom including but not limited to human beings and "mammal" refers to all mammals, including, but not limited to human beings.

As used herein, "treatment" or "treating" of a wound or defect means administration to a patient by any suitable dosage regimen, procedure and/or administration route of a composition, device or structure with the object of achieving a desirable clinical/medical end-point including attracting progenitor cells, healing a wound, correcting a defect, etc.

As used herein, the terms "cell" and "cells" refer to any types of cells from any animal, such as, without limitation, rat, mouse, monkey, and human. For example and without limitation, cells can be progenitor cells, e.g., pluripotent cells, including stem cells, induced pluripotent stem cells, multi-potent cells, or differentiated cells, such as endothelial cells and smooth muscle cells. In certain aspects, cells for medical procedures can be obtained from the patient for autologous procedures, or from other donors for allogeneic procedures. Stem cells useful for ligament repair include mesenchymal stem cells (MSCs) or adipose-derived stromal/stem cells (ASCs), tendon and ligament progenitor cells, induced pluripotent stem cells and their derived cell lines, endothelial stem cells, tenocytes, ligamentocytes, and others. Methods of identifying, isolating and preparing cells, including stem cells and induced stem cells, are broadly-known.

A "cell growth scaffold" is a mesh, matrix, particle, or surface upon which or into which a cell can be deposited and can be maintained in a living state, and often propagates (multiplies) in the presence of a cell growth medium.

As used herein, the term "polymer composition" is a composition comprising one or more polymers. As a class, "polymers" includes, for example and without limitation, homopolymers, heteropolymers, copolymers, block co-polymers and can be both natural and synthetic. Homopolymers contain one type of building block, or monomer, whereas copolymers contain more than one type of monomer. Polymers can have any shape, including, without limitation: linear, branched, star-shaped, comb-shaped, and dendrimeric.

A polymer "comprises" or is "derived from" a stated monomer if that monomer is incorporated into the polymer. Thus, the incorporated monomer that the polymer comprises is not the same as the monomer prior to incorporation into the polymer, in that at the very least, during incorporation of the monomer, certain groups, e.g., terminal groups, that are modified during polymerization are changed, removed, and/or relocated, and certain bonds may be added, removed, and/or modified. A monomer may be a "macromer", and oligomer or polymer that is the combination product of two or more smaller residues, and is employed as a monomer in preparation of a larger polymer. An incorporated monomer is referred to as a "residue" of that monomer. A polymer is said to comprise a specific type of linkage if that linkage is present in the polymer, thus, a polyester comprises a plurality of ester linkages, a polyurethane comprises a plurality of urethane (e.g., carbamate) linkages, and a poly(ester urethane) urea comprises ester, urethane, and urea linkages. Unless otherwise specified, molecular weight for polymer compositions refers to weight average molecular weight ($M_W$). Composition of a copolymer may be expressed in terms of a ratio, typically a molar ratio, of incorporated monomers or as a feed ratio of monomers prior to polymerization. In the case of feed ratios, the relative amount of each monomer incorporated into the copolymer is influenced by reaction kinetics, and the nature of the chemical reaction(s) employed to join the monomers. A "moiety" is a portion of a molecule, compound or composition, and includes a residue or group of residues within a larger polymer.

A bioerodible polymer is a polymer that degrades in vivo over a time period, which can be tailored to erode over a time period ranging from days to months, and up to two years, for example, a polymeric structure, when placed in vivo, will degrade within a time period of up to two years. By "bioerodible," it is meant that a polymer, once implanted and placed in contact with bodily fluids and/or tissues, will degrade either partially or completely through chemical, biochemical, and/or enzymatic processes, as compared to non-bioerodible polymers. Non-limiting examples of such chemical reactions include acid/base reactions, hydrolysis reactions, and enzymatic cleavage. In certain aspects, the biodegradable polymers may comprise homopolymers, copolymers, and/or polymeric blends comprising, without limitation, one or more of the following monomers: glycolide, lactide, caprolactone, dioxanone, and trimethylene carbonate. In other non-limiting embodiments, the polymer(s) comprise labile chemical moieties, non-limiting examples of which include esters and anhydrides, which can be useful in, for example and without limitation, controlling the degradation rate of the prosthetic ligaments described herein and/or the release rate of therapeutic agents, such as the extract described herein, from the cell growth scaffold (e.g., matrix or mesh) or particles used to form the ligament or tendon structure.

A "ligament structure" or a "tendon structure" is an artificial or natural ligament or tendon (respectively), such as a natural or synthetic polymer fiber or porous matrix (e.g., a cell growth scaffold), typically in the shape of a ligament, tendon, or a portion thereof, or a natural ligament, including autologous ligament or a cadaveric ligament.

A composition is "free" of a stated constituent if that constituent is not present in the composition or is present in insubstantial amounts that do not interfere, or that insignificantly interfere, with intended use and function of the composition.

By "biocompatible," it is meant that a polymer composition and its normal degradation in vivo products are cytocompatible and are substantially non-toxic and non-carcinogenic in a patient within useful, practical and/or acceptable tolerances. By "cytocompatible," it is meant that the polymer can sustain a population of cells and/or the polymer composition, device, and degradation products thereof are not cytotoxic and/or carcinogenic within useful, practical, and/or acceptable tolerances. For example, the polymer when placed in a human epithelial cell culture does not adversely affect the viability, growth, adhesion, and number of cells. In one non-limiting embodiment, the compositions and/or devices are "biocompatible" to the extent they are acceptable for use in a human or veterinary patient according to applicable regulatory standards in a given jurisdiction. In another example, the biocompatible polymer, when implanted in a patient, does not cause a substantial adverse reaction or substantial harm to cells and tissues in the body, for instance, the polymer composition or device does not cause unacceptable inflammation, allergic reaction, necrosis, or an infection resulting in harm to tissues from the implanted scaffold.

Compositions may comprise a pharmaceutically acceptable carrier, or excipient. An excipient is an inactive substance used as a carrier for the active ingredients of a medication. Although "inactive," excipients may facilitate and aid in increasing the delivery, stability or bioavailability of an active ingredient in a drug product. Non-limiting examples of useful excipients include: anti-adherents, binders, rheology modifiers, coatings, disintegrants, emulsifiers, oils, buffers, salts, acids, bases, fillers, diluents, solvents, flavors, colorants, glidants, lubricants, preservatives, antioxidants, sorbents, vitamins, sweeteners, etc., as are available in the pharmaceutical/compounding arts.

In the Example below, the healing potential of extracts of ACL and PCL is examined by testing them on stem cells and focusing on stem cell differentiation and proliferation. PCL extracellular matrix (ECM) soluble fraction is shown to have superior tenogenic function, even when compared to a fraction prepared by the same method obtained from the ACL.

The described ligament ECM soluble fraction or extract, e.g., a PCL and ACL ECM soluble fraction or extract, is expected to be useful in the fields of orthopedics and dentistry. For orthopedics, cruciate ligament partial or full tears are major issues, the extract described herein is expected to significantly promote regeneration and repair. Rotator cuff ligaments are also often injured with limited success in complete regeneration. For dentistry, during tooth avulsion, the periodontal ligament anchoring the tooth to the alveolar socket is completely torn. Tooth avulsion is a major issue especially for adolescent and young adults in sports with limited options for repair, one of the limitations being the regeneration of the periodontal ligament. It is believed that the extract will be helpful in promoting periodontal ligament regeneration.

Thus, described herein is a tissue-specific, soluble extract derived from ligament ECM that can be used to promote periodontal ligament regeneration. The extracts are cell-free and nucleic acid-free (DNA-free and RNA-free), and promote and enhance the specific differentiation of stem cells towards a tenogenic phenotype characteristic of native ligament and tendon cells. The extract can be applied to promote the regeneration of ligaments and tendons, such as joint tendons, for example the periodontal ligament that secures back in place an avulsed tooth, to improve the outcomes of replantation, decrease the risk of failure, and eliminate costs associated with implant and prosthodontic therapies.

The compositions and methods described herein comprise a soluble tissue extract (e.g., fraction) prepared from decellularized tissue, for example and without limitation, by incubating decellularized, nuclease-treated tissue, e.g., ligament tissue, such as cruciate ligament tissue, or PCL tissue, in a solubilizing reagent, such as 1 M to 8M, e.g., 3M urea—referred to herein, for example, as the ECM soluble fraction, and similar terms. Nuclease-treated decellularized tissue has lower nucleic acid content than non-nuclease-treated decellularized tissue, and typically negligible amounts of nucleic acid, e.g., DNA-free and RNA-free, digested with DNase and RNase to substantially or completely digest all DNA and RNA, in the recited tissue.

According to one aspect of the invention a composition is provided comprising a soluble fraction of decellularized, nucleic acid-free ligament tissue (referred to herein as ligament ECM soluble fraction). The ligament tissue used to prepare the composition may be obtained from a different species (xenogeneic), the same species (allogeneic), or from the same individual (autologous), in relation to a specific patient. In one aspect, the ligament tissue is posterior cruciate ligament (PCL) tissue. As used herein, unless identified as human, "PCL" includes the caudal cruciate ligament of the stifle, or knee, of other mammals, including quadrupeds, e.g., in humans, cows, horses, pigs, sheep, and dogs, and equivalents of either.

A "fraction" of a tissue or ECM is a portion of the material forming decellularized tissue that is separated from a different portion of the decellularized tissue or ECM by any suitable method, including by centrifugation, filtration, chromatography, size exclusion, affinity, or any other method. In reference to the compositions described herein, and hydrogels in general, by "soluble fraction," it is meant the water-soluble fraction of decellularized tissue or ECM, and which can be separated from an insoluble fraction by, e.g., centrifugation. Decellularized tissue or ECM obtained from ligaments, is primarily composed of fibrillar collagen, and includes other high-molecular weight proteins, glycosaminoglycans and proteoglycans present, including small leucine-rich proteoglycans such as decorin, fibromodulin and biglycan and collagen oligomeric matrix protein (COMP) (see, e.g., Birch, H L, et al. Specialisation of extracellular matrix for function in tendons and ligaments (2013) *Muscles Ligaments Tendons J.* 3(1): 12-22). Removal of the insoluble constituents, such as by centrifugation, fractionates the decellularized tissue or ECM material into a soluble supernatant and an insoluble pellet. In one aspect, the soluble fraction is "fibrillar collagen free" because fibrillar collagen is a major part of the insoluble fraction of ECM. A "soluble fraction" of decellularized tissue or ECM material can be prepared by any method of releasing soluble constituents from decellularized tissue or ECM. Examples of protein solubilizing reagents other than urea that are useful for releasing soluble constituents from decellularized tissue include, guanidinium salts, thiourea, sodium dodecyl sulfate, strong bases, strong acids, many of which are strong denaturing agents that are likely to destroy bioactivities of the ECM constituents when used at high concentrations. The protein solubilizing reagents ("solubilizing reagents") are used in amounts or concentrations that break interactions involved in protein aggregation, which include disulfide bonds, hydrogen bonds, van der Waals forces, ionic interactions, and hydrophobic interactions. Such solubilizing reagents, e.g. denaturants, are therefore used at concentrations that do not permanently disrupt the bioactivity of the constituents in the context of its end-use, e.g., ability of the constituents to promote ligament growth, for example as shown in the Example, once the denaturant is removed from the solution, such as by dialysis or by column chromatography.

In one aspect, the soluble fraction is prepared by the following method (see, Yang, G., et al. Enhancement of tenogenic differentiation of human adipose stem cells by tendon-derived extracellular matrix. *Biomaterials* 34, 9295, 2013), exemplified in Example 1, below:

Comminute ligament tissue. This can be performed by any useful method, e.g., as described above, and in one aspect, ligament tissue is frozen, sectioned in a cryostat (e.g., 40 µm thick sections), and pulverized in liquid nitrogen to form a powder;

Decellularize the tissue in any useful manner, including, e.g., protease digestions (e.g., Trypsin-EDTA) and treatment with a surfactant and/or emulsifier, e.g., with a non-ionic detergent such as TRITON X-100 (2-[4-(2,4,4-trimethylpentan-2-yl)phenoxy]ethanol), e.g. at 1% in water;

Digest nucleic acids in the sample, e.g., by treatment with DNAse and RNAse;

Dissociating soluble components from insoluble components by exposure of the sample to a solubilizing reagent, such as, for example and without limitation, a chemical denaturant, such as urea, guanidinium salts, or thiourea, a surfactant, such as sodium dodecyl sulfate, strong bases, strong acids, for example and without limitation, urea at 1M-8M or from 1.5M to 5M, e.g., 3M urea; however, denaturing agents that can destroy bioactivities of the ECM molecules when used at high concentrations, and as-such are used at non-denaturing concentrations.

Fractionate the sample into a soluble fraction and an insoluble fraction, e.g., by centrifugation or otherwise, to remove collagen and other insoluble ECM macromolecules;

Collect the soluble fraction, such as the supernatant if the sample is centrifuged in the previous step;

Remove the denaturant, e.g., by dialyzing against water or by column chromatography;

Optionally concentrate the sample, such as by spin concentration; and

Sterilize the sample, e.g., by filter sterilization with a 0.22 µm filter.

In aspects, the ligament ECM soluble fraction is administered to a patient at a site of ligament or tendon repair, injury, growth, regeneration, etc. For example, it can be injected into a patient at a site of a damaged ligament, such as in an injured ACL, PCL, ankle, or tooth socket, in an amount effective to stimulate regrowth of ligament tissue in a patient. In one aspect, the ligament ECM soluble fraction is applied to a root surface of an avulsed tooth. In another aspect, the ligament ECM soluble fraction is injected at a site of a damaged ligament, such as a partially torn, or torn ACL, PCL, or other ligament. In another aspect, the ligament ECM soluble fraction is coated onto, contained within or injected into a ligament structure, such as a porous polymer structure as described herein. In another aspect, the ligament ECM soluble fraction is coated onto, and/or injected into an autograft ligament that is implanted in a patient. In a further aspect, the ligament ECM soluble fraction is coated onto or injected into a cadaver (e.g., allograft) ligament that is implanted in a patient. In a further aspect, the ligament ECM soluble fraction is absorbed or encapsulated into or onto microparticles or nanoparticles, and is then injected, coated, or otherwise applied at a site of ligament or tissue repair in a patient, such as in a tooth socket, or at the site of a ligament injury.

In yet another aspect, the ligament ECM soluble fraction is combined with fibrin or fibrinogen, and is then injected at a site of ligament or tissue repair in a patient, such as in a tooth socket, or at the site of a ligament injury. For example, in one aspect, the ligament ECM soluble fraction is combined with a fibrin glue, as are commercially available, such as EIVCEL® fibrin sealant (Ethicon) or TISSEEL (Baxter). A fibrin glue typically comprises in a first vial or medical syringe (examples of vessels), fibrinogen, Factor XIII and fibronectin, and in a second vial or syringe, thrombin, which may be lyophilized or in a liquid state. The ligament ECM soluble fraction is contained in the first and/or second vial or syringe, and optionally is contained within or on microparticles or nanoparticles. In use, where the components are lyophilized, they are first reconstituted in water or another suitable, sterile aqueous solvent, such as normal saline (0.9% w/v saline) or PBS, or they are used in lyophilized form. Once reconstituted, if necessary, the contents of the first and second vessel (e.g., vial or medical syringe) are mixed, such as in a common mixing chamber, and are delivered to a site of a patient, such as at the site of a ligament or tendon tear, reattachment of a completely torn ligament or tendon, or insertion of a ligament or tendon structure, for example and without limitation, for gluing an avulsed tooth into a periodontal pocket.

In one aspect, the ligament ECM soluble fraction is used as a therapeutic by itself, optionally in combination with other active agents, such as an antibiotic (e.g., ARESTIN®, e.g., minocycline HCl, e.g., in microspheres, for an avulsed tooth) and/or a thickening agent. In another aspect, it is combined with or encapsulated within other structures or compositions, for example in a controlled-release structure, such as a porous or fibrous matrix of synthetic or natural bioerodible polymers, non-erodible polymers, and/or ECM products, such as an ECM material, such as decellularized, nuclease-treated tissue, or a gel prepared therefrom, and in examples, other than native ligament tissue. Other compositions with which the ligament ECM soluble fraction may be combined include hydrogels comprising natural or synthetic polymer compositions, or viscous compositions comprising suitable rheology modifiers. In one aspect, the ligament ECM soluble fraction is combined with a fibrin gel or fibrin glue. In another aspect, the ligament ECM soluble fraction is combined with a methacrylated gelatin (GelMA), which can be printed to form a 3D structure. In another aspect, the ligament ECM soluble fraction is combined with a thickening or rheology-modifying agent, such as carboxymethylcellulose, or a thixotropic agent. In any aspect, the ligament ECM soluble fraction is dispersed within, contained within, absorbed into or adsorbed to a particle, such as a micro- or nano-particle, such as a hydrogel bead comprising any suitable polymer composition and/or ECM composition, for example, as described below. In a further aspect, the ligament ECM soluble fraction is contained within a porous particle, such as a microparticle or nanoparticle, such as a hydrogel particle that can be formed by any process, such as by mixing the ligament ECM soluble fraction with a hydrogel polymer composition, followed by crosslinking of the polymer composition, or by pre-forming the hydrogel particle and absorbing or adsorbing the ligament ECM soluble fraction into the particle. A microparticle refers to a particle having a size, such as a diameter, in the range of from one to 999 microns and a nanoparticle refers to a particle having a size, such as a diameter, in the range of from one to 999 nanometers.

Particles can be used to produce a delayed release effect, for release of the soluble ECM fraction over a suitable extended time period, ranging from hours to months. A large number of microparticles and nanoparticles are known and are effective for drug delivery, and would be effective for delivery and extended release of the soluble PCL ECM fraction as described herein (see, e.g., Xiaojiao Yu, et al. "Design of Nanoparticle-Based Carriers for Targeted Drug Delivery," *Journal of Nanomaterials*, vol. 2016, Article ID 1087250, 15 pages, 2016. doi:10.1155/2016/1087250; Rajesh Singh, et al., "Nanoparticle-based targeted drug delivery" *Exp Mol Pathol*. 2009 June; 86(3): 215-223.

doi:10.1016/j.yexmp.2008.12.004; Polymers for Drug Delivery (2015) Sigma-Aldrich Co. LLC; and, generally, Xuan Ding et al., "Extended Release and Targeted Drug Delivery Systems", in *Remington The Science and Practice of Pharmacy*, David B. Troy Ed. 2006 Lippincott Williams & Wilkins, Chapter 47).

Non-limiting examples of a bioerodible polymer useful for tissue or ligament growth scaffolds, hydrogels, or particles for delivery of the ligament ECM soluble fraction include: a polyacrylate or polymethacrylate, a polyacrylamide or polymethacrylamide, a polyester, a polyester-containing copolymer, a polyanhydride, a polyanhydride-containing copolymer, a polyorthoester, and a polyorthoester-containing copolymer. In one aspect, the polyester or polyester-containing copolymer is a poly(lactic-co-glycolic) acid (PLGA) copolymer. In another embodiment, the bioerodible polymer is selected from the group consisting of poly(lactic acid) (PLA); poly(trimethylene carbonate) (PTMC); poly(caprolactone) (PCL); poly(glycolic acid) (PGA); poly(glycolide-co-trimethylenecarbonate) (PGTMC); poly(L-lactide-co-glycolide) (PLGA); polyethylene-glycol-(PEG-) containing block copolymers; and polyphosphazenes. Additional bioerodible, biocompatible polymers include: a poly(ester urethane) urea (PEUU); poly(ether ester urethane)urea (PEEUU); poly(ester carbonate)urethane urea (PECUU); poly(carbonate)urethane urea (PCUU); a polyurethane; a polyester; a polymer comprising monomers derived from alpha-hydroxy acids such as: polylactide, poly(lactide-co-glycolide), poly(L-lactide-co-caprolactone), polyglycolic acid, poly(dl-lactide-co-glycolide), and/or poly(l-lactide-co-dl-lactide); a polymer comprising monomers derived from esters including polyhydroxybutyrate, polyhydroxyvalerate, polydioxanone, and/or polyglactin; a polymer comprising monomers derived from lactones including polycaprolactone; or a polymer comprising monomers derived from carbonates including polycarbonate, polyglyconate, poly(glycolide-co-trimethylene carbonate), or poly(glycolide-co-trimethylene carbonate-co-dioxanone).

Non-limiting examples of natural bioerodible polymers useful for tissue or ligament growth scaffolds or particles include proteins, glycosaminoglycans, and polysaccharides, such as, without limitation, cross-linked or non-cross-linked: heparin, alginate (alginic acid), guar gum, carboxymethylcellulose (CMC), hyaluronic acid, pullulan, carrageenan, pectin, acid modified chitosan, xanthan gum, agarose, chitosan, collagen, elastin, cellulose, hyaluronic acid, and gelatin, or a mixture of two or more of any of the foregoing. Synthetic and/or natural polymer compositions may be cross-linked by any of a large variety of known crosslinking methods, using any of the large variety of known crosslinkers. For example, gelatin and/or hyaluronan crosslinked with methacrylate to produce methacrylated gelatin and/or hyalyronan, e.g., by photocrosslinking.

Non-bioerodable polymers either do not erode substantially in vivo or erode over a time period of greater than two years. Compositions such as, for example and without limitation, polytetrafluoroethylene (PTFE), poly(ethylene-co-vinyl acetate), poly(n-butylmethacrylate), poly(styrene-b-isobutylene-b-styrene), and polyethylene terephthalate are considered to be non-bioerodable polymers. Other suitable non-bioerodable polymer compositions are broadly known in the art, for example, in stent coating and transdermal reservoir technologies. The growth scaffolds described herein may comprise a non-erodible polymer composition.

Methods of preparation of polymeric compositions described herein are broadly-known. For example, diamines and diols are useful building blocks for preparing certain polymer compositions. Diamines have the structure $H_2N$—R—$NH_2$ where, e.g., "R" is an aliphatic or aromatic hydrocarbon or a hydrocarbon comprising aromatic and aliphatic regions. The hydrocarbon may be linear or branched. Examples of useful diamines are putrescine (R=butylene) and cadaverine (R=pentylene). Useful diols include polycaprolactone (e.g., Mw 1000-5000), multi-block copolymers, such as polycaprolactone-PEG copolymers, including polycaprolactone-b-polyethylene glycol-b-polycaprolactone triblock copolymers of varying sizes. Other building blocks for useful diols include, without limitation glycolides (e.g., polyglycolic acid (PGA)), lactides, dioxanones, and trimethylene carbonates. Diisocyanates have the general structure OCN—R—NCO, where, e.g., "R" is an aliphatic or aromatic hydrocarbon or a hydrocarbon comprising aromatic and aliphatic regions. The hydrocarbon may be linear or branched.

Additional polymers and polymerization methods may be employed to produce a useful bioerodible or non-erodible composition. For example, acrylate or methacrylate monomers, such as, for example and without limitation, N-isopropylacrylamide, acrylic acid, methacrylic acid, and/or hydroxyethyl methacrylate can be polymerized by free-radical polymerization or living polymerization methods, such as atom transfer radical polymerization. Ionic polymerization methods may also be utilized to produce useful polymer compositions. The preceding examples of polymer compositions and methods of making polymer compositions are merely illustrative of the many polymer compositions useful for tissue engineering and regenerative medicine applications and are not intended to be limiting.

For illustration, examples of suitable bioerodible polymers include PEUU, PEEUU, PCUU, and PECUU. PEUU can be synthesized using putrescine as a chain extender and a two-step solvent synthesis method. For example, a poly(ester urethane) urea elastomer (PEUU) may be made from polycaprolactonediol (MW 2,000) and 1,4-diisocyanatobutane, with a diamine, such as putrescine as the chain extender. A suitable PEUU polymer may be made by a two-step polymerization process whereby polycaprolactone diol (Mw 2,000), 1,4-diisocyanatobutane, and putrescine are combined in a 1:2:1 molar ratio, though virtually any molar feed ratio may suffice so long as the molar ratio of each monomer component is >0. In one embodiment, the molar feed ratio of polycaprolactone diol plus putrescine is equal to that of diisocyanatobutane. In the first polymerization step, a 15 wt % solution of 1,4-diisocyanatobutane in DMSO is stirred continuously with a 25 wt % solution of diol in DMSO. In the second step, stannous octoate is added and the mixture is allowed to react at 75° C. for 3 hours, with the addition of triethylamine to aid dissolution. A poly(ether ester urethane) urea elastomer (PEEUU) may be made by reacting polycaprolactone-b-polyethylene glycol-b-polycaprolactone triblock copolymers with 1,4-diisocyanatobutane and putrescine. PEEUU may be obtained by a two-step reaction using a 2:1:1 reactant stoichiometry of 1,4-diisocyanatobutane:triblock copolymer:putrescine. In the first polymerization step, a 15 wt % solution of 1,4-diisocyanatobutane in DMSO is stirred continuously with a 25 wt % solution of triblock copolymer diol in DMSO. In the second step, stannous octoate is added and the mixture is allowed to react at 75° C. for 3 hours. The reaction mixture is then cooled to room temperature and allowed to continue for 18 h. The PEEUU polymer solution is then precipitated with distilled water and the wet polymer is immersed in isopropanol for 3 days to remove unreacted monomer and dried under vacuum.

PECUU and PCUU are described, for example, in Hong et al. (Tailoring the degradation kinetics of poly(ester carbonate urethane)urea thermoplastic elastomers for tissue engineering scaffolds Biomaterials, doi:10.1016/j.biomaterials.2010.02.005). PECUU is synthesized, for example, using a blended soft segment of polycaprolactone (PCL) and poly(1,6-hexamethylene carbonate) (PHC) and a hard segment of 1,4-diisocyanatobutane (BDI) with chain extension by putrescine. Different molar ratios of PCL and PHC can be used to achieve different physical characteristics. Putrescine is used as a chain extender by a two-step solvent synthesis method. In one example, the (PCL+PHC):BDI:putrescine molar ratio is defined as 1:2:1. Variable molar ratios of PCL and PHC (e.g., PCL/PHC ratios of 100/0 (yielding a PEUU), 75/25, 50/50, 25/75 and 0/100 (yielding a PCUU)) are completely dissolved in DMSO in a 3-neck flask with argon protection and then BDI is added to the solution, following 4 drops of $Sn(Oct)_2$. The polyurethane ureas synthesized from the different PCL/PHC molar ratios defined above are referred to as PEUU, PECUU 75/25, PECUU 50/50, PECUU 25/75 and PCUU, respectively. In practice, the yields of all final products using this method is approximately 95%.

Generally, any type of extracellular matrix (ECM) can be used to produce ECM products to which the soluble ECM fraction described above is added or combined. ECM materials are prepared, for example, from decellularized or devitalized ECM material, that optionally has not been dialyzed. ECM materials are broadly-known, and are commercially-available in many forms, and may be prepared from a natural ECM (tissue), or from an in vitro source wherein the ECM is produced by cultured cells and comprises one or more polymeric components (constituents) of native ECM. ECM can be engineered into a variety of three-dimensional structures (See, e.g., Wade, et al. "Engineering ECM Signals Into Biomaterials" *Materials Today*, 2012; 15(10):454-459). In aspects ECM is isolated from a vertebrate animal, for example, from a warm blooded mammalian vertebrate including, but not limited to, human, monkey, pig, cow, horse, or sheep. The ECM may be derived from any organ or tissue, including without limitation, connective tissue such as ligaments and tendons, urinary bladder, intestine, liver, heart, esophagus, spleen, cartilage, meniscus, bone, stomach and dermis. Tissue for preparation of ECM as described herein may be harvested in any useful manner. According to various aspects, the ECM materials described herein are prepared from any suitable tissue, such as connective tissue, such as ligaments or tendons. For example and without limitation, in one aspect, the ECM material, e.g., for use in preparation of an ECM gel, is prepared from harvested ACL or PCL ligament, other ligaments, tendons, or other tissue. The ECM can comprise any portion or tissue obtained from an organ, including, for example and without limitation, and where relevant, submucosa, epithelial basement membrane, tunica propria, etc. The ECM material may take many different forms, though in the context of ligament repair, is a fiber, a bundle of fibers, or ligament-shaped. The matrix can be affixed in place at the site of implantation using a medically acceptable adhesive or sutures.

As used herein, the terms "extracellular matrix" and "ECM" refer to a natural composition useful for cell growth. ECM is decellularized or devitalized tissue, and is a complex mixture of structural and non-structural biomolecules, including, but not limited to, proteins, glycosaminoglycans, proteoglycans, antimicrobials, chemoattractants, cytokines, and growth factors, such as collagens, elastins, and laminins. In mammals, ECM often comprises about 90% collagen in its various forms. The composition and structure of ECMs vary depending on the source of the tissue. For example, ligament, small intestine submucosa (SIS), urinary bladder matrix (UBM), liver stroma ECM, and dermal ECM each differ in their overall structure and composition due to the unique cellular niche needed for each tissue.

As used herein, the term "derive" and any other word forms or cognates thereof, such as, without limitation, "derived" and "derives", refers to a component or components obtained from any stated source by any useful method. For example and without limitation, generically, material or an ECM-derived gel refers to a material or gel comprised of components of ECM obtained from any tissue by any number of methods known in the art for isolating ECM. In another example, mammalian tissue-derived ECM refers to ECM comprised of components of a particular mammalian tissue obtained from a mammal by any useful method.

Decellularized or devitalized ECM can be dried, either lyophilized (freeze-dried) or air dried. For preparation of the soluble fraction described herein, or for preparation of a gel to be combined with the soluble fraction, the ECM material or tissue used for preparation of the ECM material is comminuted, e.g. powdered. Material can be comminuted by any useful method, such as by grinding, crushing, or milling in a frozen or freeze-dried state. As used herein, the term "comminute" and any other word forms or cognates thereof, such as, without limitation, "comminution" and "comminuting", refers to the process of reducing larger particles, e.g., of dried ECM or tissue, into smaller particles, including, without limitation, by tearing, grinding, blending, shredding, slicing, milling, cutting, shredding, shearing, and pulverizing. ECM can be comminuted while in any form, including, but not limited to, hydrated forms, frozen, air-dried, freeze dried/lyophilized, or in sheet-form.

Tissue for preparation of ECM as described herein may be harvested in any useful manner. According to various aspects, the ECM materials described herein are prepared from any suitable tissue, such as connective tissue such as ligaments or tendons. For example and without limitation, in one aspect, the ECM material, e.g., for use in preparation of an ECM gel, is prepared from harvested ACL or PCL ligament, other ligaments, tendons, or other tissue.

ECM gels for combination with the soluble ECM fraction, can be prepared by a number of methods, such as, without limitation, by acid-protease digestion, urea treatment, and cross-linking of solubilized ECM materials by the addition of reactive groups followed by chemical crosslinking, such as by photopolymerization using, e.g., photo-initiators and UV light. In aspects, an ECM gel is reverse gelling, or can be said to exhibit reverse thermal gelation, in that it forms a gel upon an increase in temperature. As the temperature rises above a certain temperature in a reverse gel, a hydrogel is formed. The general concept of reverse gelation of polymers is broadly known in the chemical arts (see, e.g., U.S. Pat. Nos. 8,361,503 and 8,691,276, U.S. Patent Application Publication Nos. 2015/0010510 and 2017/0173217, and International Patent Application Publication No. WO 2017/123883, each of which is incorporated herein by reference for its technical disclosure). The ECM gel can be molded into a defined shape, or formed into particles, e.g., by spraying or comminution in a dried state, and, e.g., reconstituted with the soluble ECM fraction as described herein.

In one aspect, an ECM gel to be combined with the soluble ECM fraction is prepared by digestion of the ECM material, in aspects non-dialyzed ECM material, with an acid protease in acidic conditions, neutralization of the material to form a pre-gel, and then raising the temperature of the pre-gel above a gelation temperature, for example, the lower critical solution temperature (LCST) of the pre-gel, to cause the pre-gel to form a gel. Other methods of producing an ECM gel, such as by urea treatment may be employed (see, e.g., Rothrauff, B. B., et al. "Efficacy of Thermoresponsive, Photocrosslinkable Hydrogels Derived from Decellularized Tendon and Cartilage Extracellular Matrix for Cartilage Tissue Engineering" *J Tissue Eng Regen Med.* 2018 January; 12(1):e159-e170). As used herein, the term "gel" includes hydrogels. The transition temperature for acid-protease-digested ECM from solution to gel is typically within the range of from 10° C. to 40° C., and any increments or ranges therebetween, for example, from 20° C. to 35° C. For example, the pre-gel can be warmed to, and forms a gel, at 37° C.

In one aspect, in order to prepare a solubilized ECM material for preparation of a gel with which the soluble ECM fraction provided herein can be mixed, ECM, for example, comminuted ECM material that has not been dialyzed, is digested with an acid protease in an acidic solution to form a digest solution. As used herein, the term "acid protease" refers to an enzyme that cleaves peptide bonds, wherein the enzyme has increased activity of cleaving peptide bonds in an acidic pH. A non-limiting example of a suitable acid protease is pepsin. As an example, the digest solution of ECM material is kept at a constant stir for a certain amount of time at room temperature. In one aspect, the pH is maintained at less than pH 4.0 or at pH 2.0±0.3 during acid protease digestion of the decellularized tissue. The ECM digest can be used immediately or can be stored at −20° C. or frozen at, for example and without limitation, −20° C. or −80° C. In certain aspects, the ECM digest is snap frozen in liquid nitrogen. To form a "pre-gel solution", the pH of the digest solution is raised to a pH between 6.8 and 7.8. The pH can be raised by adding one or more of a base or a buffer, such as an isotonic buffered solution, for example and without limitation, NaOH or PBS at pH 7.4. The method optionally does not include a dialysis step prior to gelation, yielding a more-complete ECM-like matrix that typically gels at 37° C. more slowly than comparable collagen or dialyzed ECM preparations. The ECM may be partially or completely digested with the acid protease, such as pepsin. The degree of digestion of the ECM can be determined by comparison on a gel, or by ascertaining the degree of degradation of hyaluronic acid, for example, by Western blot (anti-hyaluronic acid antibodies are commercially-available from multiple sources) or chromatographic methods, as are broadly known. For example, in a partial digestion, hyaluronic acid is digested less than 50%, 40%, 30%, 25%, 20%, or 10%. As indicated above, the digested ECM is neutralized to a pH of 6.8-7.8, e.g., 7.2-7.6, or 7.4 to produce a pre-gel solution, and the pre-gel solution is gelled by incubation at a temperature at which the material gels, e.g., at a temperature above 20°, 25°, 30°, or 35° C., such as at 37° C.

Cell growth matrices and ligament or tendon structures can be formed by any useful method, for example by solvent casting in a mold, typically with particulate leaching to produce a porous structure, or by 3D printing or dry spinning methods, or by electrodeposition. In one aspect, the structure is cut from a polymeric mesh comprising synthetic and/or natural (e.g., ECM) polymer compositions. In one aspect, for illustrative purposes, a polymeric mesh is electrodeposited, e.g., electrospun onto a target, such as a mandrel, and the resultant structure is shaped, e.g., by cutting, into a suitable ligament shape, or a shape of a portion of a ligament to be repaired (see, for example, U.S. Pat. Nos. 8,535,719 B2 and 9,237,945 B2, and United States Patent Application Publication No. 2014/0377213 A1, each of which is incorporated herein by reference in its entirety for their disclosure of electrospinning methods, and variations on electrospun matrices, including synthetic and natural components). While the polymeric mesh may be isotropic, the nature of ligament ECM often is anisotropic, and as such, the polymeric mesh that is used to prepare the prosthetic ligament is deposited in an oriented manner, and is therefore anisotropic. Electrospinning and electrodeposition methods are broadly-known, and in electrodeposition, relative movement of the nozzles/spinnerets and target surface, e.g., by deposition onto a rotating mandrel, during electrodeposition can be used to produce an oriented pattern of fibers. As is further broadly-known more than one polymer composition can be electrodeposited concurrently, or in a desired order, to create a layered structure. Further, solutions comprising other polymers, ECM materials (e.g., ECM gel, or solubilized ECM), cell-culture medium, cells, such as stem cells including MSCs or ASCs, blood products, therapeutic agents, and the PCL ECM soluble fraction as described herein, can be electrosprayed onto, or into the formed fiber structure, with variable deposition timing to create optimal layering or release of the soluble fraction. In aspects, the PCL soluble fraction is applied to a formed fiber matrix, and optionally can be mixed with an ECM pre-gel, or a bioerodible polymer solution, prior to deposition, e.g., electrospraying, or for application to a fiber matrix after formation of the fiber matrix by dipping, soaking, or otherwise contacting the fiber matrix with the PCL ECL soluble fraction.

The properties of electrospun elastomeric matrices can be tailored by varying the electrospinning conditions. For example, when the biased target is relatively close to the orifice, the resulting electrospun mesh tends to contain unevenly thick fibers, such that some areas of the fiber have a "bead-like" appearance. However, as the biased target is moved further away from the orifice, the fibers of the non-woven mesh tend to be more uniform in thickness. Moreover, the biased target can be moved relative to the orifice. In certain embodiments, the biased target is moved back and forth in a regular, periodic fashion, such that fibers of the non-woven mesh are substantially parallel to each other. When this is the case, the resulting non-woven mesh may have a higher resistance to strain in the direction parallel to the fibers, compared to the direction perpendicular to the fibers. In other embodiments, the biased target is moved randomly relative to the orifice, so that the resistance to strain in the plane of the non-woven mesh is isotropic. The target can also be a rotating mandrel. In this case, the properties of the non-woven mesh may be changed by varying the speed of rotation. The properties of the electrospun elastomeric scaffold may also be varied by changing the magnitude of the voltages applied to the electrospinning system.

Electrospinning may be performed using two or more nozzles, wherein each nozzle is a source of a different polymer solution. The nozzles may be biased with different biases or the same bias in order to tailor the physical and chemical properties of the resulting non-woven polymeric mesh. Additionally, many different targets may be used. In addition to a flat, plate-like target, a mandrel may be used as a target. When the electrospinning is to be performed using a polymer suspension, the concentration of the polymeric component in the suspension can also be varied to modify the physical properties of the elastomeric scaffold. For example, when the polymeric component is present at relatively low concentration, the resulting fibers of the electrospun non-woven mesh have a smaller diameter than when the polymeric component is present at relatively high concentration. One skilled in the art can adjust polymer concentrations to obtain fibers of desired characteristics. Useful ranges of concentrations for the polymer component include from about 1% wt. to about 15% wt., from about 4% wt. to about 10% wt. and from about 6% wt. to about 8% wt.

In electrospinning, polymer fibers are often deposited about the circumference of a mandrel and to generate a planar or substantially planar structure, the electrodeposited mat/matrix is cut substantially in the direction of the rotational axis of the mandrel, or in any manner to generate a useful topology, such as the shape of a ligament or portion thereof. In use, more than one electrospun mats/matrices can be attached by any useful means, such as by "sewing" using sutures, heat annealing, chemical annealing/cross-linking, etc., though it should be recognized that the method of attaching the two or more mats/matrices would have to be strong enough for the end use, e.g., to resist breakage, rupture, or herniation.

Although any form of spraying is expected to be effective, liquid, e.g. cell growth media, ECM pre-gel, cells, a blood product, such as serum, plasma, or platelet-rich plasma, or a therapeutic composition, such as the soluble PCL ECM fraction described herein, may be electrosprayed. Electrospraying can be done before, after, or concurrently (intermittently or continuously) with the electrodeposition of polymer fibers, and is conducted in an essentially identical manner.

In use, the structures described herein are surgically-implanted, e.g., at the site of a ligament repair. Methods of implanting the materials are known in the art and are a matter of using standard surgical techniques, such as for suturing a ligament in place.

The composition and structures according to any aspect described herein can also can include an active agent, such as, without limitation, one or more of an antiseptic, an antibiotic, an analgesic, an anesthetic, a chemotherapeutic agent, an anti-inflammatory agent, a metabolite, a cytokine, a chemoattractant, a hormone, a steroid, a protein, or a nucleic acid. Therapeutic agents that may be incorporated, by themselves, or in combination with a suitable excipient, into the compositions described herein include, without limitation, anti-inflammatories, such as, without limitation, NSAIDs (non-steroidal anti-inflammatory drugs) such as salicylic acid, indomethacin, sodium indomethacin trihydrate, salicylamide, naproxen, colchicine, fenoprofen, sulindac, diflunisal, diclofenac, indoprofen sodium salicylamide, antiinflammatory cytokines, and antiinflammatory proteins or steroidal anti-inflammatory agents); growth factors; antibiotics, such as, without limitation: acyclovir, afloxacin, ampicillin, amphotericin B, atovaquone, azithromycin, ciprofloxacin, clarithromycin, clindamycin, clofazimine, dapsone, diclazaril, doxycycline, erythromycin, ethambutol, fluconazole, fluoroquinolones, foscarnet, ganciclovir, gentamicin, iatroconazole, isoniazid, ketoconazole, levofloxacin, lincomycin, miconazole, minocycline (e.g., minocycline HCl, or ARESTIN® microspheres for periodontal use), neomycin, norfloxacin, ofloxacin, paromomycin, penicillin, pentamidine, polymixin B, pyrazinamide, pyrimethamine, rifabutin, rifampin, sparfloxacin, streptomycin, sulfadiazine, tetracycline, tobramycin, trifluorouridine, trimethoprim sulphate, Zn-pyrithione, ciprofloxacin, norfloxacin, afloxacin, levofloxacin, gentamicin, tobramycin, neomycin, erythromycin, trimethoprim sulphate, polymixin B, and silver salts such as chloride, bromide, iodide and periodate.

Any useful cytokine or chemoattractant can be mixed into, mixed with, or otherwise combined with any composition as described herein. For example and without limitation, useful components include growth factors, interferons, interleukins, chemokines, monokines, hormones, and angiogenic factors. In certain non-limiting aspects, the therapeutic agent is a growth factor, such as a neurotrophic or angiogenic factor, which optionally may be prepared using recombinant techniques. Non-limiting examples of growth factors include basic fibroblast growth factor (bFGF), acidic fibroblast growth factor (aFGF), vascular endothelial growth factor (VEGF), hepatocyte growth factor (HGF), insulin-like growth factors 1 and 2 (IGF-1 and IGF-2), platelet derived growth factor (PDGF), stromal derived factor 1 alpha (SDF-1 alpha), nerve growth factor (NGF), ciliary neurotrophic factor (CNTF), neurotrophin-3, neurotrophin-4, neurotrophin-5, pleiotrophin protein (neurite growth-promoting factor 1), midkine protein (neurite growth-promoting factor 2), brain-derived neurotrophic factor (BDNF), tumor angiogenesis factor (TAF),corticotrophin releasing factor (CRF), transforming growth factors α and β (TGF-α and TGF-β), interleukin-8 (IL-8), granulocyte-macrophage colony stimulating factor (GM-CSF), interleukins, and interferons. Commercial preparations of various growth factors, including neurotrophic and angiogenic factors, are available from R & D Systems, Minneapolis, Minnesota; Biovision, Inc, Mountain View, California; ProSpec-Tany TechnoGene Ltd., Rehovot, Israel; and Cell Sciences®, Canton, Massachusetts.

In certain non-limiting aspects, the therapeutic agent is an angiogenic therapeutic agent. Non-limiting examples of angiogenic therapeutic agents include: erythropoietin (EPO), basic fibroblast growth factor (bFGF), acidic fibroblast growth factor (aFGF), fibroblast growth factor-2 (FGF-2), granulocyte colony stimulating factor (G-CSF), granulocyte macrophage colony stimulating factor (GM-CSF), hepatocyte growth factor (HGF), insulin-like growth factors 1 and 2 (IGF-1 and IGF-2), placental growth factor (PlGF), platelet derived growth factor (PDGF), stromal derived factor 1 alpha (SDF-1 alpha), vascular endothelial growth factor (VEGF), angiopoietins (Ang 1 and Ang 2), matrix metalloproteinase (MMP), delta-like ligand 4 (Dll4), and class 3 semaphorins (SEMA3s), all of which are broadly-known, and are available from commercial sources.

Other drugs that may promote wound healing and/or tissue regeneration may also be included.

Example 1

The soluble component of anterior and posterior cruciate ligament extracellular matrix (ACL ECM and PCL ECM for brevity) were prepared, and their effects were compared on proliferation and tenogenic differentiation of stem cell. The rest of the ECM (the insoluble fraction, mainly collagen) which provides structure and a scaffold, is discarded and not used in this work. Unexpectedly, result indicate that PCL ECM has higher potential for both proliferation and tenogenic differentiation of stem cells. This is unexpected because the two ligaments are generally regarded as very similar and our own SDS-PAGE analysis of the two extracts' compositions did not show any obvious difference. If anything, being the ACL partially vascularized, the opposite result would have been expected, hence the higher capacity to induce tenogenic differentiation of stem cells (differentiation towards a ligament/tendon cell phenotype) by PCL ECM is totally serendipitous.

The ligament ECM extracts can be used in the fields of orthopedics, craniofacial and plastic surgery, and dentistry. For orthopedics, cruciate ligament partial or full tears are major issues and the extract is expected to significantly promote regeneration and repair. Rotator cuffs ligaments are also often injured with limited success in complete regeneration. For dentistry, during tooth avulsion the periodontal ligament anchoring the tooth to the alveolar socket is completely torn—tooth avulsion is a major issue especially for adolescent and young adults in sports with limited options for repair, one of the limitation being the regeneration of the periodontal ligament. The extract is expected to have the ability to promote periodontal ligament regeneration.

Bovine ACL, PCL, and infrapatellar fat pad were harvested within 24 hours of slaughter. Soluble ECM components of ACL and PCL were urea-extracted. To obtain ECM powder, ligaments were minced into fine pieces with a scalpel and scissors and frozen at −80° C. The frozen ligament pieces were pulverized in liquid nitrogen with a mortar pestle or a mechanical milling device, and the tissue powder was then decellularized by incubation in 1% Triton X-100 (Sigma-Aldrich) in phosphate-buffered saline, pH 7.4 (PBS) under continuous agitation for 24 h at 4° C., followed by three washes, 30 min each in PBS. The decellularized material was then treated with 200 U/ml DNase and 50 U/ml RNase (Worthington, Lakewood, NJ) solution at 37° C. for 12 h and then washed in PBS 6 times, 30 min for each wash. After nuclease digestion, the preparation was extracted with 3 M urea (Sigma-Aldrich) in water with gentle agitation for 3 days at 4° C. The suspension was then centrifuged for 20 min at 1,500 g to collect the extract supernatant. Urea was removed by dialysis of the extract contained in dialysis cassettes (3,500 MWCO, Thermo Scientific, Rockford, IL) against PBS for 2 days at 4° C. Water was changed every 4 h. The dialyzed ECM extract was transferred into centrifugal filter tubes (3,000 MWCO, Millipore, Carrigtwohill, Ireland) and spin-concentrated by 10 folds for 30 min at 1,500 g. The final ECM solution was filter-sterilized through PVDF syringe filter units (0.22 μm, Millipore), protein concentration determined using the BCA assay (Thermo Scientific), and then stored at 4° C. until further use. Total proteins were extracted from homogenized original ligament tissues by TM buffer (Total Protein Extraction Kit, Millipore) and served as a control.

On average, 10 ml of soluble ECM were obtained from 5 g of ligament tissue. Protein concentration was determined by the BCA assay (Thermo Scientific) and then adjusted to 800 mg/ml by dilution. Soluble ECM samples were analyzed by SDS-PAGE on pre-cast NuPAGE gels in MOPS SDS running buffer, and gels were stained with SimplyBlue SafeStain (Coomassie G-250). bASCs were isolated from minced infrapatellar fat pad by collagenase type I digestion. To reduce individual variation, fat pads from the 3 bovines were pooled. bASCs were cultured in growth medium (DMEM-high glucose, 10% fetal bovine serum (FBS), 100 units/ml penicillin and 100 mg/ml streptomycin, Gibco). All experiments were performed with passage 2 bASCs. Cells were seeded on 24 well plates at 10 cells/well and cultured for 7 days under three different conditions: growth medium (GM) only, GM+10% (v/v) of ACL ECM solution, and GM+10% (v/v) of PCL ECM solution. Media were renewed every 3 days. On days 1, 3 and 7, MTS assay (CellTiter 96AqueousOne Solution Cell Proliferation Assay, Promega), Picogreen assay (Quant-iT PicoGreen dsDNA Reagent, Invitrogen), and Live/Dead assay (Thermo Scientific) were performed to determine cell viability (N=6 per group, per time point) as per the manufacturers' protocol. At each time point, total RNA was isolated using an RNA extraction Kit (Qiagen) according to the manufacturer's protocol. First-strand cDNA was synthesized with oligo(dT) primers using a cDNA synthesis kit (Invitrogen). Quantitative real-time PCR was performed using SYBR green Supermix in a Step One Plus real-time PCR system (Applied Biosystem, Life Technology) and then analyzed by the $C_T$ (ΔΔCt) method, to assess expression of tenogenesis marker genes including scleraxis (SCX), tenomodulin (TNMD), tenascin-C (TNC), decorin (DCR), and collagen I (COL I). For statistical analysis, ANOVA followed by a post hoc test with significance at $p<0.05$ was used.

Figure 2:
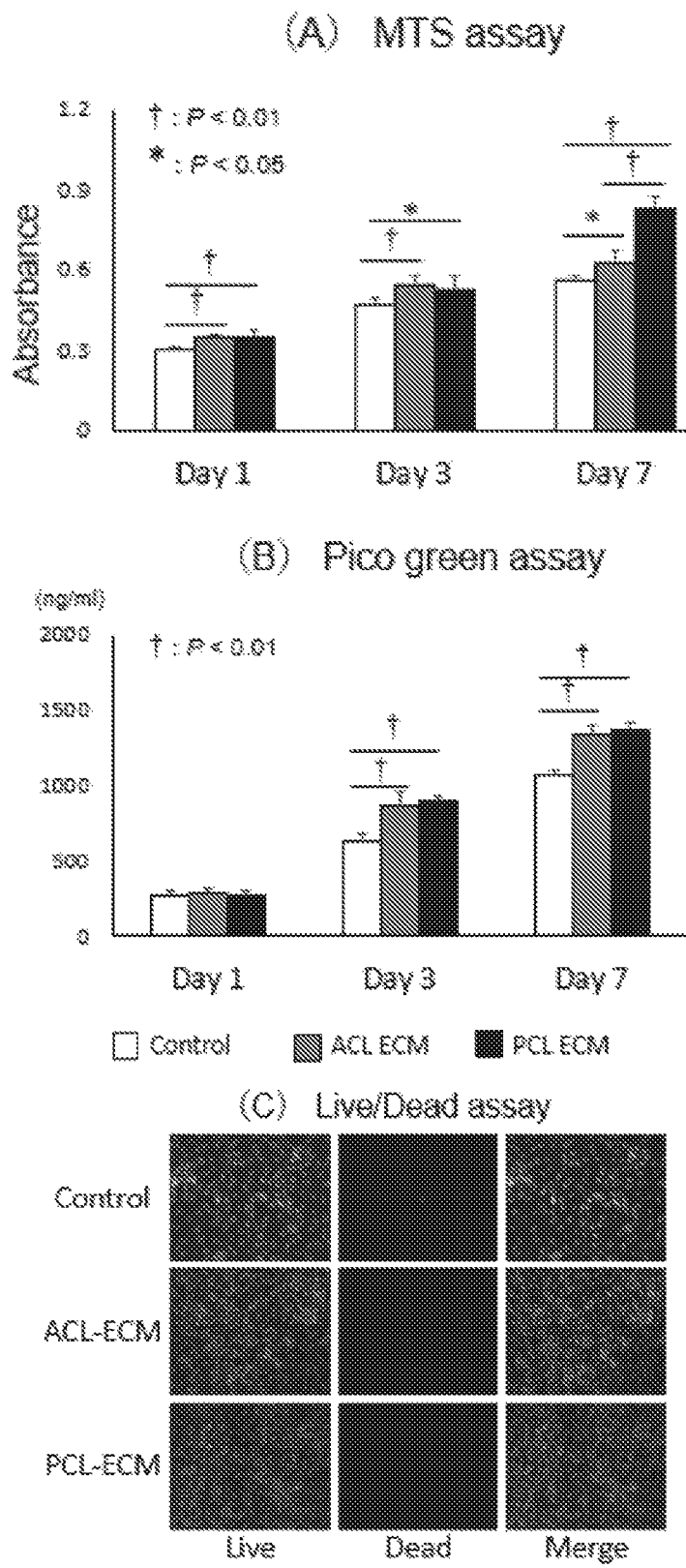
FIG. 2. Panels (A) and (B) are graphs showing MTS assay and Picogreen staining, respectively, as described in Example 1. Panel (C) are photomicrographs showing cell viability, as described in Example 1.

SDS-PAGE analysis revealed that ACL and PCL ECM contained a high amount of low molecular weight (<100 KD) protein components, with no apparent difference between the two (FIG. 1). At days 1, 3 and 7, cell metabolic activity and cell numbers were determined by MTS assay and Picogreen staining, respectively (FIGS. 2A and B). Cells seeded with ACL and PCL ECM significantly increased metabolic activity and cell number compared to control, suggesting that the presence of ligament ECM promoted cell proliferation and cell activity. After 7 days of culture, cells retained good viability (FIG. 2C).

Figure 3:
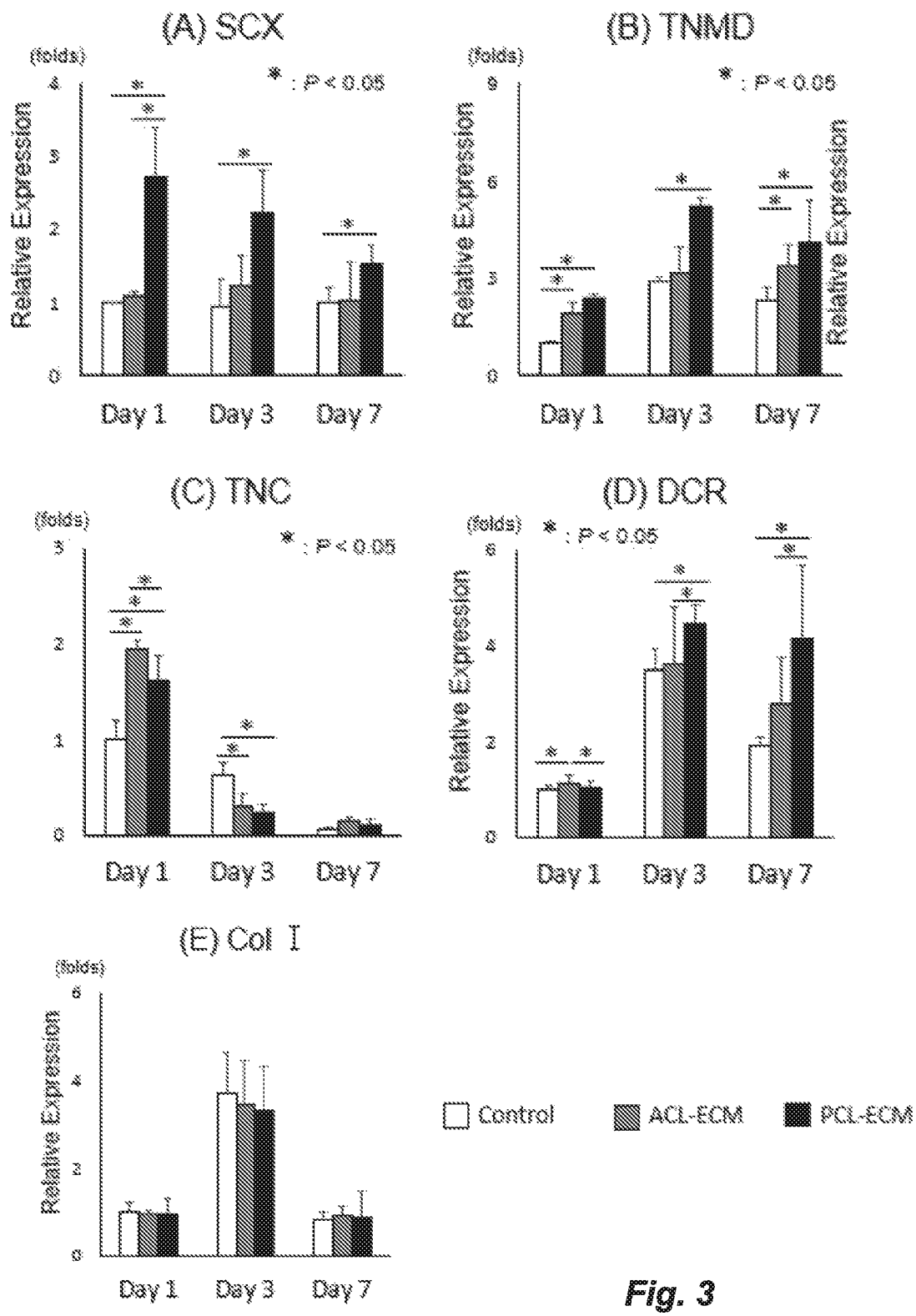
FIG. 3. Panels (A) through (E) provide graphs showing relative expression of the indicated genes, as described in Example 1.

The expression of SCX was significantly higher in the PCL ECM group compared to the ACL ECM and control groups at all time points (FIG. 3A). The expression of TNMD was significantly higher than control in both the ACL and PCL ECM groups at days 1 and 7. The expression of TNC was initially higher in both the ACL and PCL ECM groups, but they all decreased faster than control by day 3 (FIG. 3C). The expression pattern of DCR was similar to that of SCX for days 3 and 7 (FIG. 3D), while COL I expression showed no significant difference between the 3 groups (FIG. 3E).

In sum, treatment with ACL and PCL derived soluble ECM promoted cell proliferation, viability and tenogenic differentiation of bovine ASCs, representing a candidate approach to enhance cruciate ligaments repair after tear. Unexpectedly, the PCL ECM extract was significantly more effective than the ACL ECM extract in promoting proliferation and differentiation of stem cells, although there was no immediate, obvious difference in their composition.

The following numbered clauses outline various aspects of the present invention.

1. A method of inducing growth of ligament or tendon tissue in a patient, comprising, administering to the patient at a site of ligament or tendon damage or defect, a composition comprising a soluble fraction of decellularized, nuclease-digested ligament tissue (soluble fraction) in an amount effective to induce growth of a ligament or tendon in a patient.

2. A method of generating or regenerating a ligament structure in a patient, comprising: implanting a ligament structure in a patient; and applying a composition comprising a soluble fraction of decellularized, nuclease-digested ligament tissue to a surface of the ligament structure, or adjacent to the ligament structure, in an amount effective to stimulate growth of a ligament.

3. The method of clause 1 or 2, wherein the decellularized, nuclease-digested ligament tissue is decellularized, nuclease-digested cruciate ligament tissue.

4. The method of clause 1 or 2, wherein the decellularized, nuclease-digested ligament tissue is decellularized, nuclease-digested posterior cruciate ligament (PCL) tissue.

5. The method of any one of clauses 1-4, wherein the composition is lyophilized prior to use.

6. The method of any one of clauses 1-5, further comprising, applying the soluble fraction to a ligament structure or a tendon structure, and implanting the ligament structure or tendon structure in the patient at the site of ligament or tendon damage or defect.

7. The method of clause 6, wherein the ligament structure or tendon structure is a polymer matrix, an autologous ligament or tendon graft, or a cadaveric ligament or tendon graft, and in one aspect is a polymer matrix comprising a natural or synthetic polymer, and optionally comprising a natural polymer, such as heparin, alginate (alginic acid), guar gum, carboxymethylcellulose (CMC), hyaluronic acid, pullulan, carrageenan, pectin, acid modified chitosan, xanthan gum, agarose, chitosan, collagen, elastin, cellulose, hyaluronic acid, or gelatin, or a mixture of two or more of any of the foregoing.

8. The method of any one of clauses 1-7, wherein the soluble fraction is soluble in 1 M-8M urea in water.

9. The method of clause 8, wherein the soluble fraction is soluble in 3M urea in water.

10. The method of clause 9, wherein the soluble fraction is solubilized in an aqueous solution of urea.

11. The method of any one of clauses 1-9, wherein the soluble fraction is prepared by removing fibrillar collagen from the decellularized, nuclease-digested PCL tissue.

12. The method of clause 11, wherein the fibrillar collagen is removed by centrifugation.

13. The method of any one of clauses 1-12, wherein the patient has an avulsed tooth, and the comprising applying the composition to a root of an avulsed tooth of the patient and/or to the periodontal pocket of the patient.

14. The method of any one of clauses 1-12, wherein the damaged or defective ligament or tendon is a knee ligament.

15. The method of clause 14, wherein the knee ligament is an ACL, PCL, meniscofemoral ligament, or MCL.

16. The method of any one of clauses 1-12, wherein the damaged or defective ligament or tendon is a hip, ankle, shoulder, wrist, elbow, spine, knee, face, or neck ligament.

17. The method of any one of clauses 1-16, wherein the composition further comprises a fibrin glue.

18. The method of any one of clauses 1-17, wherein the soluble fraction of the decellularized, nuclease-digested ligament tissue composition is dispersed within a controlled-release structure.

19. The method of clause 18, wherein the controlled-release structure comprises a porous or bioerodible polymer.

20. The method of clause 18, wherein the controlled-release structure is a particle, such as a microparticle or a nanoparticle, such as a polymer microparticle or a nanoparticle.

21. The method of clause 18, wherein the controlled-release structure comprises fibrin, fibrin glue, or methacrylated gelatin.

22. The method of any one of clauses 1-21, wherein the soluble fraction of the decellularized, nuclease-digested ligament tissue is prepared by:
  comminuting ligament tissue;
  optionally freezing and thawing the tissue prior to, during, or after the comminuting;
  decellularizing the tissue in a detergent or emulsifier, for example, in a non-ionic detergent such as TRITON X-100, for example at 1% in water;
  digest nucleic acids in the decellularized tissue, e.g., by treatment with DNAse and optionally RNAse;
  dissociating soluble components from insoluble components by exposure of the sample to, for example and without limitation, a chemical denaturant, such as urea, a guanidinium salt, thiourea, sodium dodecyl sulfate, strong bases, strong acids, for example, 1M to 8M urea or 3M urea in water;
  fractionating the composition, e.g., by centrifugation or otherwise, to remove insoluble fibrillar collagen, thus collecting the soluble fraction, such as the supernatant
  remove the denaturant from the soluble fraction, e.g., by dialyzing against water or by column chromatography, such as by size-exclusion chromatography;
  optionally concentrating the soluble fraction, such as by spin concentration;
  optionally sterilizing the soluble fraction, e.g., by filter sterilization with a 0.22 µm filter; and
  optionally lyophilizing the soluble fraction.

23. The method of clause 22, wherein, prior to dissociating the soluble components, the tissue is not decellularized with a protease, such as pepsin or trypsin.

24. A composition comprising a urea-soluble fraction of decellularized, nuclease-digested ligament tissue, and a pharmaceutically-acceptable excipient.

25. The composition of clause 24, wherein the ligament tissue is cruciate ligament tissue, or posterior cruciate ligament tissue.

26. The composition of clause 24, wherein the composition is dried.

27. The composition of any one of clauses 24-26, wherein the soluble fraction is free of fibrillar collagen.

28. The composition of any one of clauses 24-27, wherein the soluble fraction is free of DNA, and optionally the extract is free of RNA.

29. The composition of any one of clauses 24-28, wherein the soluble fraction is soluble in 3M urea in water.

30. The composition of any one of clauses 24-28, wherein the soluble fraction is solubilized in 1 M-8M urea in water.

31. The composition of any one of clauses 24-30, further comprising fibrin or fibrinogen.

32. The composition of any one of clauses 24-30, dispersed within or on, or contained within or on a controlled-release structure.

33. The composition of clause 32, wherein the controlled-release structure is a particle, such as a microparticle or a nanoparticle.

34. The composition of clause 32, wherein the controlled-release structure comprises a natural or synthetic bio-erodible polymer composition and/or an ECM composition.

35. A ligament structure comprising a cell growth scaffold that is optionally anisotropic, and a urea-soluble fraction of nuclease-digested, decellularized ligament tissue, such as cruciate ligament tissue or posterior cruciate ligament tissue.

36. The ligament structure of clause 35, further comprising stem cells, such as an MSCs or ASCs, on or within the cell growth scaffold of the ligament structure.

37. The ligament structure of clause 35 or 36, wherein the soluble fraction is soluble in 3M urea in water.

38. The ligament structure of any one of clauses 35-37, wherein the soluble fraction is solubilized in 1M to 8M urea in water.

39. The ligament structure of any one of clauses 35-38, wherein the soluble fraction is free of fibrillar collagen.

40. The ligament structure of any one of clauses 35-37, wherein the soluble fraction of decellularized, nuclease-digested posterior cruciate ligament tissue is dispersed within or on, or contained within or on, a controlled release structure 41. The ligament structure of clause 40, wherein the controlled-release structure is a particle, such as a polymer micro-particle or nano-particle.

42. A method of preparing a composition for stimulating ligament growth, comprising:
comminuting ligament tissue;
decellularizing the tissue in a detergent or emulsifier, for example, in a non-ionic detergent such as TRITON X-100, e.g. at 1% in water;
digest nucleic acid in the decellularized tissue by treatment of the decellularized tissue with a nuclease, such as a DNAse or an RNAse;
dissociating soluble components from insoluble components by exposure of the sample to a protein solubilizing reagent, such as urea, a guanidinium salt, thiourea, sodium dodecyl sulfate, a strong base, or a strong acid, for example, 1M to 8M urea, for example 3M urea in water;
fractionating the composition, e.g., by centrifugation or chromatography, to separate a soluble fraction from insoluble fibrillar collagen, and collecting the soluble fraction, such as the supernatant; and
removing the denaturant from the soluble fraction, e.g., by dialyzing against water or by column chromatography, such as by size-exclusion chromatography.

43. The method of clause 42, comprising:
freezing the tissue;
powdering the tissue while frozen;
decellularizing the tissue in TRITON X-100 in water;
digesting the decellularized tissue with DNAse and RNAse to produce a substantially nucleic acid free decellularized tissue;
dissociating soluble components from insoluble components by exposure of the sample to 2-8M urea, e.g., 3M urea;
centrifuging the decellularized tissue to produce a collagen-containing pellet and a supernatant comprising a soluble fraction of the decellularized tissue; and
dialyzing the supernatant, e.g., against water, to remove urea from the supernatant.

44. The method of clause 42, further comprising:
freezing and thawing the tissue prior to, during, or after the comminuting;
concentrating the soluble fraction, such as by spin concentration;
sterilizing the soluble fraction, e.g., by filter sterilization with a 0.22 μm filter; or
lyophilizing the soluble fraction.

45. A method of preparing a ligament structure, comprising applying a soluble fraction of nuclease-digested, decellularized ligament tissue, such as cruciate ligament tissue, such as PCL tissue to a cell growth matrix, optionally an anisotropic cell growth matrix.

46. The method of clause 45, wherein the soluble fraction is electrosprayed onto, or co-electrodeposited with, the cell growth matrix.

47. A kit comprising a composition according to any of clauses 24-34 in a vessel, such as a vial or medical syringe, wherein the composition is optionally lyophilized.

48. The kit of clause 47, further comprising fibrinogen or thrombin in the vessel.

49. The kit of clause 47, wherein the composition is dispersed within or on, or contained within or on a particle, such as a microparticle or a nanoparticle.

50. The kit of clause 47, wherein the particle comprises a natural or synthetic bio-erodible polymer composition and/or an ECM material.

While the present invention is described with reference to several distinct embodiments, those skilled in the art may make modifications and alterations without departing from the scope and spirit. Accordingly, the above detailed description is intended to be illustrative rather than restrictive.

What is claimed is:

1. A composition comprising:
(a) a urea-soluble fraction of decellularized, nuclease-digested anterior cruciate ligament or posterior cruciate ligament tissue prepared by:
comminuting anterior cruciate ligament or posterior cruciate ligament tissue;
decellularizing the tissue in a detergent or emulsifier;
digesting nucleic acid in the decellularized tissue by treatment of the decellularized tissue with a nuclease;
dissociating soluble components from insoluble components by exposure of the digested, decellularized tissue to urea;
fractionating the dissociated, digested, decellularized tissue to separate a urea-soluble fraction from insoluble fibrillar collagen;
collecting the urea-soluble fraction; and
removing the urea from the urea-soluble fraction; and
(b) a pharmaceutically-acceptable excipient.

2. The composition of claim 1, wherein the urea-soluble fraction is free of fibrillar collagen and nucleic acid.

3. The composition of claim 1, wherein the soluble fraction is soluble in 1M-8M urea in water.

4. The composition of claim 1, dispersed within or on, or contained within or on a controlled-release structure.

5. The composition of claim 1, wherein the composition comprises a urea-soluble fraction of decellularized, nuclease-digested posterior cruciate ligament tissue.

6. A method of inducing growth of ligament or tendon tissue in a patient, comprising, administering to the patient at a site of ligament or tendon damage or defect, an effective amount of the composition of claim 1.

7. The method of claim 6, wherein the decellularized, nuclease-digested ligament tissue is decellularized, nuclease-digested posterior cruciate ligament (PCL) tissue.

8. The method of claim 6, further comprising, applying the soluble fraction to a ligament structure or a tendon structure, and implanting the ligament structure or tendon structure in the patient at the site of ligament or tendon damage or defect.

9. The method of claim 8, wherein the ligament structure or tendon structure is a polymer scaffold, an autologous ligament or tendon graft, a cadaveric ligament or tendon graft, or a cell growth scaffold that is optionally anisotropic comprising a natural and/or a synthetic polymer.

10. The method of claim 6, wherein the soluble fraction is solubilized in an aqueous solution of 1M to 8M urea.

11. The method of claim 6, wherein the soluble fraction is prepared by removing fibrillar collagen from the decellularized, nuclease-digested PCL tissue.

12. The method of claim 6, wherein the patient has an avulsed tooth, the method comprising applying the composition to a root of an avulsed tooth of the patient and/or to the periodontal pocket of the patient.

13. The method of claim 6, wherein the damaged or defective ligament or tendon is a hip, ankle, shoulder, wrist, elbow, spine, knee, face, or neck ligament.

14. The method of claim 6, wherein the composition further comprises a fibrin glue.

15. The method of claim 6, wherein the soluble fraction of the decellularized, nuclease-digested is dispersed ligament tissue composition within a controlled-release structure.

16. The method of claim 6, wherein, prior to dissociating the soluble components, the tissue is not decellularized with a protease, such as pepsin or trypsin.

17. A method of preparing a composition for stimulating ligament growth, comprising:
 combining (a) a urea-soluble fraction of decellularized, nuclease-digested anterior cruciate ligament or posterior cruciate ligament tissue and (b) a pharmaceutically-acceptable excipient;
 wherein the urea-soluble fraction is prepared by:
  comminuting anterior cruciate ligament or posterior cruciate ligament tissue;
  decellularizing the tissue in a detergent or emulsifier;
  digesting nucleic acid in the decellularized tissue by treatment of the decellularized tissue with a nuclease;
  dissociating soluble components from insoluble components by exposure of the digested, decellularized tissue to urea;
  fractionating the dissociated, digested, decellularized tissue to separate a urea-soluble fraction from insoluble fibrillar collagen;
  collecting the urea-soluble fraction; and
  removing the urea from the urea-soluble fraction.

18. A method of preparing a ligament structure, comprising applying an effective amount of a urea-soluble fraction of decellularized, nuclease-digested anterior cruciate ligament or posterior cruciate ligament tissue to a growth matrix;
 wherein the urea-soluble fraction is prepared by:
  comminuting anterior cruciate ligament or posterior cruciate ligament tissue;
  decellularizing the tissue in a detergent or emulsifier;
  digesting nucleic acid in the decellularized tissue by treatment of the decellularized tissue with a nuclease;
  dissociating soluble components from insoluble components by exposure of the digested, decellularized tissue to urea;
  fractionating the dissociated, digested, decellularized tissue to separate a urea-soluble fraction from insoluble fibrillar collagen;
  collecting the urea-soluble fraction; and
  removing the urea from the urea-soluble fraction.

19. A kit comprising a composition according to claim 1 in a vessel, such as a vial or medical syringe, wherein the composition is optionally dried or lyophilized.

* * * * *

UNITED STATES PATENT AND TRADEMARK OFFICE
CERTIFICATE OF CORRECTION

PATENT NO. : 12,070,475 B2  
APPLICATION NO. : 16/970861  
DATED : August 27, 2024  
INVENTOR(S) : Riccardo Luca Gottardi Page 1 of 1

It is certified that error appears in the above-identified patent and that said Letters Patent is hereby corrected as shown below:

On the Title Page

Column 1, Assignees, Line 4, delete "(IT)" and insert -- Palermo (IT) --

In the Claims

Column 23, Line 4, Claim 15, after "nuclease-digested" delete "is dispersed"

Column 23, Line 5, Claim 15, after "composition" insert -- is dispersed --

Signed and Sealed this  
Second Day of September, 2025

Coke Morgan Stewart  
*Acting Director of the United States Patent and Trademark Office*